United States Patent [19]

Echt et al.

[11] Patent Number: 5,051,150
[45] Date of Patent: Sep. 24, 1991

[54] STABILIZED SYNTHETIC PULP-CELLULOSE BLENDS

[75] Inventors: Elliott Echt; Edward J. Engle, III, both of New Castle County, Del.

[73] Assignee: Hercules Incorporated, Wilmington, Del.

[21] Appl. No.: 325,756

[22] Filed: Mar. 20, 1989

[51] Int. Cl.$^5$ ............................................. D21H 13/14
[52] U.S. Cl. .................................. 162/146; 162/157.5; 162/182; 264/13
[58] Field of Search ..................... 162/146, 157.5, 182; 264/13

[56] References Cited

U.S. PATENT DOCUMENTS

| | | | |
|---|---|---|---|
| 3,049,466 | 8/1962 | Erlich | 162/157.5 |
| 3,743,272 | 7/1973 | Nowotny | 264/69 |
| 3,743,570 | 7/1973 | Yang | 162/146 |
| 3,770,856 | 11/1973 | Ueki | 264/13 |
| 3,808,091 | 4/1974 | Aoki | 264/13 |
| 3,914,354 | 10/1975 | Ueki | 264/211 |
| 3,920,507 | 11/1975 | Yonemori | 162/164 |
| 3,936,512 | 2/1976 | Tabara | 264/13 |
| 3,953,282 | 4/1976 | Tabara | 162/102 |
| 3,997,648 | 12/1976 | Davis | 162/157.5 |
| 4,013,751 | 3/1977 | Davis | 162/157.5 |
| 4,110,385 | 8/1978 | Sander | 264/13 |
| 4,112,029 | 9/1978 | Sander | 264/13 |
| 4,274,917 | 6/1981 | Murphy | 162/182 |
| 4,332,749 | 6/1982 | Pleska | 264/13 |
| 4,496,427 | 1/1985 | Davison | 162/146 |
| 4,655,877 | 4/1987 | Horimoto | 264/121 |
| 4,833,011 | 5/1989 | Horimoto | 428/288 |
| 4,861,428 | 8/1989 | Van Breen | 162/146 |
| 5,000,824 | 3/1991 | Gale | 162/157.5 |

FOREIGN PATENT DOCUMENTS 261832 3/1988 European Pat. Off. ............ 162/146

Primary Examiner—Stanley S. Silverman
Assistant Examiner—Thomas M. Lithgow
Attorney, Agent, or Firm—David Edwards

[57] ABSTRACT

A stabilized synthetic polyolefin pulp-cellulose blend is prepared by adding 0.1-1.0% by weight of an antioxidant (a hindered phenolic and/or phosphite antioxidant) to a solution of a polyolefin and solvent wherein the antioxidant is homogenously dispersed therein, forming the polyolefin into a polyolefin pulp, and then mixing the polyolefin pulp with from about 55 to about 90% by weight of a wood pulp to produce the blend. This blend with improved higher ignition temperature is used in the absorbent products industry as an absorbent core, when the blend is heated sufficiently to melt the polyolefin.

6 Claims, No Drawings

STABILIZED SYNTHETIC PULP-CELLULOSE BLENDS

BACKGROUND OF THE INVENTION

This invention relates to a blend of a polyolefin pulp and wood pulp stabilized by an antioxidant.

Prior to the present invention, it was found that blends of synthetic polyolefin pulp and wood pulp when heated in air produced a significant exotherm at a temperature lower than either of the exotherm temperatures of the individual components. This created a potential problem in the absorbent product industry that processed blends of this type for various products because an uncertainty was created of whether, or not, such mixtures may be easily ignited. Hence, a need exists in the industry for producing blends of synthetic polyolefin pulp and wood pulp that are stabilized to higher ignition temperatures.

Although no prior art was found that dealt with the specific problem mentioned above, a few publications were found that used synthetic pulp blends for absorbent applications. European Application 261,832 discloses a fibrous molded article having 5-50 wt. % of a pulp fiber of a thermoplastic resin and 50-95 wt. % of a second hydrophilic short fiber whereas the pulp fiber has on its surface a composition of a propylene glycol (a surfactant) stabilized with at least one stabilizer selected from phenolic antioxidant and phosphorus acid ester type antioxidant. Japanese Patent Application 58,208,496 and U.S. Pat. No. 4,245,689 disclose a base paper composition of a cellulose fiber, a glass fiber, and/or a synthetic fiber such as polyethylene. In each of these publications, the composition is impregnated with a high polymer emulsion such as a rubber latex; each of these references also discloses that antioxidants can be present.

None of the above mentioned prior art discloses the instant invention.

SUMMARY OF THE INVENTION

The present invention is directed to a method of preparing a stabilized polyolefin blend comprising:

a) forming a slurry comprising polylolefin and solvent (e.g., pentane or hexane), b) adding antioxidant that is compatible with the polyolefin to said slurry, said antioxidant being employed in an amount of from 0.1-1.0% by weight, based on the weight of polyolefin, c) heating the slurry to form a homogeneous solution of the polyolefin and antioxidant in the solvent, d) forming the polyolefin solution into a polyolefin pulp, and e) mixing the polyolefin pulp with from about 55 to about 90% by weight, based on the total weight of the blend, of a wood pulp to produce the stabilized pulp blend.

This invention also comprehends the product prepared by the above mentioned method.

DETAILED DESCRIPTION OF THE INVENTION

It has recently been found that the use of polyolefin synthetic pulp as a binder in absorbent products is an application that requires a high level of stabilizer to prevent the exothermic reaction of wood pulp/polyolefin mixtures at relatively low temperatures and in a short time. The stabilizer is incorporated into a solution of a polyolefin dissolved in a solvent to produce a homogeneous solution. This homogeneous solution is then made into a synthetic pulp from the solution where the stabilizer is dispersed uniformly throughout the synthetic pulp. This resulting pulp with the high percentage of stabilizer protects against the exothermic reaction in the presence of wood pulp. Also, the stabilizer by being incorporated directly into the polyolefin will be protected against various wet process losses during the manufacture of synthetic pulp and/or the wet laid combination of synthetic pulp with wood pulp, in contrast to a stabilizer present on the pulp surface.

A high level of stabilizer is defined as being from about 0.1% to about 1.0% (preferably 0.1 to about 0.4%) by weight based on the total weight of the synthetic pulp. It is critical that this high level of stabilizer be incorporated directly into the polyolefin because the processing of polyolefin pulp, wood pulp blends are usually carried out in the absorbent industry at elevated temperatures; even for short periods of time, this may be hazardous. The elevated temperature may, for instance, be generated by friction when defibering (i.e., fluffing) the blends in a hammermill. The general range of the synthetic pulp-wood pulp blends of the present invention is from about 5% to about 50% (by weight) for the synthetic pulp with the preferred range being from about 15% to about 30% by weight. Accordingly, the range of the wood pulp would be from about 50% to about 95%, preferably from about 70% to about 85%.

The type of stabilizers used in this invention are thioether antioxidants, hindered phenolic antioxidants and/or phosphite antioxidants. Examples of thioether antioxidants are dilauryl thiodipropionate (DLTDP) and distearyl thiodipropionate ((DSTDP). Hindered phenolic antioxidants are sterically hindered phenols that undergo fast reactions with peroxy radicals. Examples of hindered phenolic antioxidants are thiobisphenols, alkylidene-bisphenols, alkylphenols, hydroxybenzyl compounds, acylaminophenols, and hydroxyphenols proprionates. Examples of phosphite antioxidants are triesters of phosphoric acid.

Examples of the polymers from which the polyolefin pulps are made are polyethylene, polypropylene, poly(4-methylpentene-1), copolymers of ethylene and 1-butene, 1-hexene, and 1-octene, copolymers of ethylene and propylene, and copolymers of propylene and other olefins such as 1-butene and 1-hexene. The polyolefin pulps can be composed solely of one of these polymers or they can be composed of mixtures of two or more of the polymers.

Synthetic pulps generally are defined as very fine, highly branched, discontinuous, water-dispersible fibers made from polymers. Polyolefin synthetic pulps may be blended in all proportions with wood pulp and made into papers and boards using conventional papermaking equipment or made into low density products by air forming. The sheets so produced may be heated to melt the polyolefin, depending on the intended application. In either event, the resulting materials differ significantly from the 100% plastic sheets or mats of continuous fibers made by many different processes. The main processes used to prepare synthetic polyolefin pulps are solution flash spinning, emulsion flash spinning, melt extrusion/fibrillation, and shear precipitation.

The process used most commonly for preparing the synthetic polyolefin pulps of this invention comprises adding the stabilizer(s) to a slurry of polymer in a suitable solvent, heating the slurry to dissolve the polymer, and forming a synthetic pulp from that solution by allowing it to expand from a high pressure to atmospheric pressure through a suitable device for forming the desired pulp structure. This technique is called solution flash spinning and is well known in the art. See, e.g., "Pulp, Synthetic," Kirk-Othmer, Encyclopedia of Chemical Technology, 3rd ed. (New York: 1982) Vol. 19, pp. 420-435.

The preferred polyolefin of this invention is high density polyethylene and the preferred stabilizer is a combination of 0.125% by weight of the polyethylene of Irgafos 168 and 0.125% by weight of the polyethylene of Irganox 1010; both of these products are marketed by Ciba-Geigy and Irgafos is a phosphite and Irganox is a hindered phenolic antioxidant. This synthetic polyolefin pulp containing the antioxidant(s) is then blended in the usual fashion with wood fluff and processed in the conventional manner of the industry. For example, the polyolefin pulp is dispersed in a hydropulper and separately the wood pulp is dispersed in another hydropulper. The two pulps are then blended together in a stock chest of a paper machine and then formed into a sheet and dried at temperatures controlled so as not to melt the polyolefin.

A suitable surface treatment can even be applied to make the desired end product absorbent after the synthetic pulp has been used as a binder. See U.S. Pat. No. 4,458,042 that discloses surface treatment of spurted polyolefin pulp.

Wood pulp can be obtained from well known chemical processes such as the kraft and the sulfite processes. For these processes, the best starting material is prepared from long fiber coniferous wood species, such as pine, douglas fir, blue fir, spruce, and hemlock. Wood pulp also can be obtained from mechanical processes, such as ground wood, refiner mechanical, thermomechanical, chemimechanical, and chemithermomechanical pulp processes. Details of the production and use of wood pulp are well known in the art.

EXAMPLES

High density polyethylene ("HDPE") pulp used in the following Examples were prepared by the solution flash spinning method. First, 9-12% by weight of high density polyethylene in pentane is made into a slurry by rapid agitation. To this slurry, 0.125% by weight of polyethylene of Irgafos 168 and Irganox 1010 is added. This slurry is then pressurized to 1,800-2,000 psig and heated to 145°-155° C. This uniform solution was then passed into a specially designed spurting nozzle or spinneret, in which a controlled pressure drop was effected. Two liquid phases, one of which was polymer-rich and the other polymer-lean, resulted. This two-phase mixture exited through a small orifice at high shear into a chamber of low temperature and approximately atmospheric pressure to quickly and completely evaporate or flash the solvent. Vaporization of solvent provided the energy to form the fibrous product, and the resulting cooling caused rapid crystallization of the HDPE pulp. Under commercial conditions, the solvent would be condensed and reused. The various HDPE pulps with different amounts of antioxidant stabilizers were then tested "as is" or wet-formed into sheets with wood pulp when testing mixtures of synthetic pulp and wood pulp.

All of the HDPE pulp products in the examples were surface treated with a suitable treatment for absorbent product end use, unless otherwise noted. Percentages of synthetic pulp are by weight based on the total blend composition unless otherwise noted. In the examples, the wood pulp used was a commercially available southern softwood kraft fluff pulp ("SKFP"). Percentages of stabilizer are by weight based on synthetic pulp.

Trademarks or tradenames used in this application for stabilizers have the following generic name:

Irgafos 168 is tris (2,4-di-tert-butyphenyl)phosphite;

Irganox 1010 is tetrakis[methylene (3,5-di-tert-butyl-4-hydroxy-hydrocinnamate)]methane;

Irganox 1076 is octadecyl 3,5-di-tert-butyl-4-hydroxyhydrocinnamate;

B-225 is a 1:1 blend of the Irgafos 168 and Irganox 1010;

B-215 is a 2:1 blend of the Irgafos 168 and Irganox 1010: and

Topanol CA is 1,1,3-tris(2-methyl-4-hydroxy-5-t-butyl phenyl)butane.

Topanol is a product of the corporation ICI Americas and the other above mentioned products are from Ciba-Geigy.

EXAMPLE I

Samples were tested for flash ignition temperature and self ignition temperature according to the method ASTM D-1919, Standard Method Test for Ignition of Plastics, Procedure B.

| Sample | Stabilizer | Flash Ignition Temp. °C. | Self Ignition Temp. °C. |
| --- | --- | --- | --- |
| A 20% HDPE pulp 80% SKFP | none | 193 | 193 |
| B 100% HDPE pulp | none | 410 | 410 |
| C 100% SKFP | none | 266 | 266 |
| D 20% HDPE pulp 80% SKFP | 0.125% Irganox 1010 0.125% Iragafos 168 | 377 | 427 |

This example shows that the flash and self ignition temperatures of the stabilized test sample D of the present invention are significantly higher than the wood pulp alone C or the unstabilized combination sample A. Sample D also has a higher self ignition temperature than sample B. These results demonstrate the unexpected results of the sample D.

EXAMPLE II

Synthetic pulps and blends of synthetic pulps with wood pulp made by a laboratory paper handsheet process were tested by being placed in an open pan in an air purge stream on a differential scanning calorimeter. These samples were heated at 10° C./min or 20° C./min. The exothermic oxidation reaction was detected by the calorimeter and the onset temperature of the exothermic reaction and the peak temperature of the reaction were used as indicators of the thermal stability of the sample, the higher those temperatures, the more stable the sample. The lower the onset and exotherm temperatures, the more rapidly the material oxidized under the test conditions.

The following table shows that the stabilized samples took longer to undergo the exotherm than the unstabilized samples. Hence, this Example shows a method of determining relative thermal stability.

| DESCRIPTION | HEATING RATE (°C./min) | SIGNIFICANT EXOTHERM PEAK, °C. |
|---|---|---|
| HDPE pulp | 20 | >330 |
| 78% SKFP 22% HDPE pulp | 20 | 243 |
| 100% SKFP | 20 | >350 |
| 10% HDPE pulp 0.1% Topanol CA 0.1% Ca stearate 90% SKFP | 20 | 267 |
| 20% HDPE pulp 0.1% Topanol CA: 0.1% Ca stearate 80% SKFP | 20 | 270 |
| 40% HDPE pulp 0.1% Topanol CA 0.1% Ca Stearate 60% SKFP | 20 | 271 |
| 100% HDPE pulp 0.1% Topanol CA: 0.1% Ca Stearate | 20 | 261 |
| 20% HDPE pulp 0.25% B-215 80% SKFP | 20 | 260 |
| 20% HDPE pulp 0.125% B-215 80% SKFP | 20 | 257 |
| 20% HDPE pulp 0.25% B-225 80% SKFP | 20 | 274 |
| 20% HDPE pulp 0.125% Irgafos 168 0.1% Topanol' 80% SKFP | 20 | 272 |
| 20% HDPE pulp 0.05% Topanol CA 0.05% Ca Stearate 80% SKFP | 20 | 258 |
| 20% HDPE pulp 0.25% Irganox 1076 80% SKFP | 20 | 263 |
| 20% HDPE pulp 0.25% Irgafos 168 80% SKFP | 20 | 245 |
| 100% HDPE pulp 0.2% Topanol CA | 20 | 252 |
| 100% HDPE pulp 0.3% Topanol Ca | 20 | 264 |
| 20% HDPE pulp 0.2% Topanol CA 80% SKFP | 20 | 273 |
| 20% HDPE pulp 0.3% Topanol CA 80% SKFP | 20 | 277 |
| 20% HDPE pulp 0.4% Topanol CA 80% SKFP | 10 | 268 |
| 20% HDPE pulp 0.4% Topanol CA 80% SKFP | 20 | 280 |
| 20% HDPE pulp 0.5% Topanol CA 80% SKFP | 10 | 270 |
| 20% HDPE pulp 0.5% Topanol CA 80% SKFP | 20 | 284 |
| 20% HDPE pulp 80% SKFP | 10 | 228 |
| 20% HDPE pulp 80% SKFP | 20 | 243 |
| 10% HDPE pulp 90% SKFP | 20 | 241 |
| 40% HDPE pulp 60% SKFP | 20 | 238 |

EXAMPLE III

This is a comparative example that tests the absorbency in pads bonded with unstabilized and stabilized HDPE pulp blends. Samples 1-6 are the unstabilized samples of 17-19% of spurted HDPE pulp with the remainder a wood pulp (marketed under the name Rayfloc J). Sample A has 20% of spurted HDPE, 80% of wood pulp, and 0.25% of B-225 stabilizer (marketed by Ciba-Geigy).

ABSORBENCY OF PADS BONDED WITH UNSTABILIZED HDPE PULP VS. STABILIZED

| SAMPLE | GSM[a] | G/CC[b] | GATS[c] ML/G | WICK HT. mm[d] (SECS.) | | | | | TENSILE[e] G/50 mm |
|---|---|---|---|---|---|---|---|---|---|
| | | | | 15 | 30 | 60 | 90 | 120 | |
| 1 | 411 | .060 | 11.04 | 34 | 36 | 37 | 38 | 39 | 1000 |
| 2 | 400 | .061 | 11.14 | 33 | 35 | 36 | 37 | 38 | 850 |
| 3 | 407 | .062 | 10.6 | 34 | 36 | 40 | 41 | 42 | 1150 |
| 4 | 202 | .055 | 12.97 | 28 | 30 | 31 | 32 | 34 | 400 |
| 5 | 205 | .059 | 12.52 | 29 | 30 | 32 | 33 | 35 | 500 |
| 6 | 204 | .058 | 11.89 | 32 | 33 | 34 | 35 | 36 | 500 |
| A | 283 | .064 | 11.43 | 40 | 51 | 58 | 62 | 64 | 825 |

[a]GSM - basis weight of the sample in grams per square meter.
[b]G/CC - density of the bonded sample in grams per square meter.
[c]GATS, ML/G - Results of testing on the Gravimetric Absorbency Testing System Model M/K301, of M/K systems, Danvers, Mass. Results are reported in milliliters of 1% saline absorbed per gram of pad.
[d]WICK HT., mm - Results of testing the vertical wicking of 1% saline solution through a 50 mm wide sample of the bonded pad suspended vertically. EDANA (European Disposables and Nonwovens Association) test method 10.0-72 part C. - Liquid Wicking Rate.
[e]TENSILE - Weights are suspended from a clamp attached to a vertically mounted sample of a bonded pad 50 mm wide. The reported weight is the total of the weights, in grams, suspended from the pad when it breaks.

The results show that the Sample A, made with the stabilized pulp, compared favorably to the other samples in total absorbency (GATS) and rate of absorbency in the vertical wicking test. The overall wick height is another indication of the wettability of sample A, and, hence, the suitability of the stabilized synthetic pulp for use in absorbent products.

What is claimed is:

1. A method of preparing a stabilized polyolefin and wood pulp blend by solution flash spinning comprising:
   a) forming a slurry comprising polyolefin and solvent,
   b) adding antioxidant that is compatible with the polyolefin to said slurry selected from the group consisting of a thioether antioxidant, a hindered phenolic antioxidant, a phosphite antioxidant, or a mixture thereof, said antioxidant being employed in an amount of from 0.1-1.0% by weight, based on the weight of polyolefin,
   c) pressurizing the slurry to 1,800-2,000 psi,
   d) heating the slurry containing said antioxidant to form a homogeneous solution of the polyolefin and antioxidant in the solvent,
   e) forming the polyolefin solution into a polyolefin pulp by
      i) passing the solution to a spurting nozzle or spinneret in which a controlled pressure drop is effected, and
      ii) flashing the solution into a chamber to quickly and completely evaporate the solvent to form the polyolefin pulp, and
   e) mixing the polyolefin pulp with from about 55 to about 90% by weight, based on the total weight of the blend, of a wood pulp to produce the stabilized pulp blend.

2. The method of claim 1 wherein the polyolefin is polyethylene.

3. The method of claim 1 wherein the polyolefin is ethylene copolymer with 1-butene, 1-hexene, or 1-octene.

4. The method of claim 2 wherein the polyethylene is high density polyethylene.

5. The product prepared by the method of claim 1.

6. The method of claim 1 wherein the solvent is pentane or hexane.

* * * * *